(12) United States Patent
Yamada et al.

(10) Patent No.: US 12,356,913 B2
(45) Date of Patent: *Jul. 15, 2025

(54) MANDEVILLA GENUS PLANT AND PRODUCTION METHOD OF SAME

(71) Applicants: SUNTORY FLOWERS LIMITED, Tokyo (JP); SUNTORY HOLDINGS LIMITED, Osaka (JP)

(72) Inventors: Masahiro Yamada, Higashiomi (JP); Tomoya Misato, Higashiomi (JP); Takehiro Watanabe, Seika-cho (JP); Toshiaki Azuma, Seika-cho (JP); Manabu Horikawa, Seika-cho (JP)

(73) Assignees: SUNTORY FLOWERS LIMITED, Tokyo (JP); SUNTORY HOLDINGS LIMITED, Osaka (JP)

(*) Notice: Subject to any disclaimer, the term of this patent is extended or adjusted under 35 U.S.C. 154(b) by 384 days.

This patent is subject to a terminal disclaimer.

(21) Appl. No.: 17/575,486

(22) Filed: Jan. 13, 2022

(65) Prior Publication Data

US 2022/0132763 A1    May 5, 2022

Related U.S. Application Data

(63) Continuation of application No. 15/322,687, filed as application No. PCT/JP2016/080617 on Oct. 14, 2016, now Pat. No. 11,252,883.

(60) Provisional application No. 62/242,025, filed on Oct. 15, 2015.

(51) Int. Cl.
*A01H 6/08* (2018.01)
*A01H 3/00* (2006.01)
*A01H 5/00* (2018.01)
*A01H 5/02* (2018.01)
*G01J 3/46* (2006.01)

(52) U.S. Cl.
CPC ............... *A01H 6/088* (2018.05); *A01H 3/00* (2013.01); *A01H 5/00* (2013.01); *A01H 5/02* (2013.01); *G01J 3/46* (2013.01)

(58) Field of Classification Search
CPC .................................................... A01H 6/088
USPC ........................................................ Plt./232
See application file for complete search history.

(56) References Cited

U.S. PATENT DOCUMENTS

| PP15,539 P2 * | 2/2005 | Misato | A01H 5/02 Plt./232 |
|---|---|---|---|
| PP22,695 P2 | 5/2012 | Misato | |
| PP24,074 P2 | 12/2013 | Lannes | |
| PP31,661 P2 * | 4/2020 | Misato | A01H 5/02 Plt./232 |
| 2004/0139501 A1 | 7/2004 | Hauptmann | |

FOREIGN PATENT DOCUMENTS

| JP | 07224029 A | 8/1995 |
|---|---|---|
| JP | 2005518805 A | 6/2005 |
| JP | 2012016314 A | 1/2012 |
| WO | 03/074670 A2 | 9/2003 |

OTHER PUBLICATIONS

Mandevilla Sanderi (Hemsl.) Woodson; "Dipladenia, Sundaville® Cream Pink," Lazdip1209. Available online at: https://www.floragard.de/Pflanzeninfothek/Pflanzen/26308-Dipladenia+'Sundaville%C2%AE+Cream+Pink'/. Accessed from the Internet on Feb. 2, 2019. 5 pages.
"Extended Search Report," mailed Mar. 4, 2019 in European Patent Application No. 16812662.1-1120 / 3363283 PCT/JP016080617. 7 pages.
Mandevilla Sanderi (Hemsl.) Woodson et al., "Technical Questions." Lazzeri Societa Agricola A R L, Community Plant Variety Office. Accessed from the Internet on Sep. 21, 2018. 15 pages.
"Final Office Action," mailed Jun. 30, 2021, in U.S. Appl. No. 15/322,687. 5 pages. Copy not provided.
"Final Office Action," mailed Aug. 9, 2019, in U.S. Appl. No. 15/322,687. 12 pages. Copy not provided.
"Non-Final Office Action," mailed Jan. 22, 2021, in U.S. Appl. No. 15/322,687. 9 pages. Copy not provided.
"Non-Final Office Action," mailed Feb. 4, 2019, in U.S. Appl. No. 15/322,687. 14 pages. Copy not provided.
"Non-Final Office Action," mailed Apr. 22, 2020, in U.S. Appl. No. 15/322,687. 14 pages. Copy not provided.
"Notice of Allowance," mailed Oct. 14, 2021, in U.S. Appl. No. 15/322,687. 7 pages. Copy not provided.
"International Search Report," mailed Jan. 10, 2017, in International Application No. PCT/JP2016/080617. 14 pages (includes English translation).
Margareth Ferreira de Sales et al., "Eight New Species of Mandevilla Lindley (Apocynaceae, Apocynoideae) from Brazil" BioONe Complete. 2006. Downloaded on Jan. 28, 2019, from: https://bioone.org/journals/Novon:-A-Journal-for-Botanical-Nomenclature. 18 pages.
Curl, Laurence A., "Structure of the Carotenoid Neoxanthin." 1965. Western Regional Research Laboratory, Western Utilization Research and Development Division Agricultural Research Service, U.S. Department of Agriculture, Albany, California. 7 pages.

(Continued)

*Primary Examiner* — David H Kruse

(74) *Attorney, Agent, or Firm* — Kilpatrick Townsend & Stockton LLP

(57) ABSTRACT

A novel *Mandevilla* genus plant is provided that has a novel color tone unable to be previously produced. A candidate *Mandevilla* genus plant is selected as a parent *Mandevilla* genus plant in the case carotenoid pigment is extracted from the petals thereof, and neoxanthin or a derivative thereof is present in the carotenoid pigment extract.

11 Claims, 11 Drawing Sheets

(56) References Cited

OTHER PUBLICATIONS

Tinoi, Jidapha et al., Determination of Major Carotenoid Constituents in Petal Extracts of Eight Selected Flowering Plants in the North of Thailand. accepted on May 15, 2006. 8 pages.

* cited by examiner

MANDEVILLA GENUS PLANT AND PRODUCTION METHOD OF SAME

CROSS-REFERENCE TO RELATED APPLICATIONS

The present application is a continuation of U.S. application Ser. No. 15/322,687, filed Dec. 28, 2016, which is a U.S. National Phase under 35 USC 371 of PCT Application No. PCT/JP2016/080617, filed Oct. 14, 2016, which application claims priority to U.S. Provisional Application No. 62/242,025, filed Oct. 15, 2015, the teaching all of which are hereby incorporated by reference in their entireties for all purposes.

TECHNICAL FIELD

The present invention relates to novel *Mandevilla* genus plant containing at least one or more types of carotenoid pigment in the petals thereof, a method for selecting a parent *Mandevilla* genus plant containing carotenoid pigment in the petals thereof and capable of crossbreeding with a *Mandevilla* genus plant having white to pink to red petals, and a method for producing a *Mandevilla* genus hybrid plant using the method for selecting a parent *Mandevilla* genus plant.

BACKGROUND ART

*Mandevilla* genus plants (also referred to as *Dipladenia*) are vine-like woody or herbaceous plants belonging to the family Apocynaceae, of which there are roughly 130 species native to tropical regions of the Americas, ranging from, for example, Mexico to Argentina.

Horticulturally, *Mandevilla×amabilis* (syns. *M. amonea*) was produced from *Mandevilla splendens* as one parent (the other parent is unknown) in the U.K. in 1868. A seedling obtained from a strain labeled "*M. amonea*" in the U.S. in 1960 flowered and became "Alice du Pont" (referred to as Rose Giant in Japan), which is widely distributed even at present (refer to the following Non-Patent Documents 1 and 2).

Until around 2000, those varieties that were distributed for horticultural purposes mainly consisted only of this "Alice du Pont", bud variations of spontaneous mutations thereof, varieties selected from seedlings obtained by open pollination, varieties selected from seedlings obtained from bud variation and open pollination with *Mandevilla sanderi* having an ambiguous history, and wild species in the form of *Mandevilla laxa* (Chilean jasmine) and *Mandevilla boliviensis* (refer to the following Patent Document 1).

Suntory Flowers Ltd. marketed a large-blooming type designated as "White" in 1998 (*Mandevilla amabilis×boliviensis* 'Sunmandeho', variety registration application no. 8721) (refer to the following Patent Document 2).

In addition, Suntory Flowers Ltd. also marketed a similar large-blooming type designated as "Big" in 2003 (*Mandevilla* hybrid 'Sunmandecos', variety registration application no. 14756) (refer to the following Patent Document 4).

Suntory Flowers Ltd. further marketed vine-blooming types in 2005 designated as "Red" (*Mandevilla hybrida* 'Sunmanderemi') (refer to the following Patent Document 5, variety registration application no. 15862) and "Tropical Peach" (*Mandevilla hybrida* 'Sunmandetomi' (refer to the following Patent Document 6), variety registration application no. 15863), while also marketing the vine-blooming type "Ruby Pink" (Sunparagropi) (variety registration application no. 24471), the vine-blooming type "Red Velvet" (*Mandevilla hybrida* 'Sunpararenga') (refer to the following Patent Document 14, variety registration application no. 23333), and the vine-blooming type (also referred to as the "Pretty" type overseas) "Sundaville Pretty Rose" (*Mandevilla hybrida* 'Sunparaprero') (refer to the following Patent Document 15).

Suntory Flowers Ltd. marketed a large-blooming type in 2007 designated as "Crimson King" (*Mandevilla hybrida* 'Sunmandecrikin') (refer to the following Patent Document 7, variety registration application no. 17409).

Suntory Flowers Ltd. also marketed a large-blooming type in the same year designated as "Crimson" (*Mandevilla hybrida* 'Sunmandecrim' (refer to the following Patent Document 3, variety registration application no. 14755).

Suntory Flowers Ltd. further marketed an early blooming type designated as "Rouge" (*Mandevilla hybrida* 'Sunmandecripi' (refer to the following Patent Document 8, variety registration application no. 23604) and "Milky Pink" (*Mandevilla hybrida* 'Sunparapibra' (refer to the following Patent Document 9, variety registration application no. 24470).

The aforementioned large-blooming type "Crimson King" and early blooming type "Crimson" are crimson *Mandevilla* varieties that had previously never existed, and as a result of the appearance of these new varieties, the market began to expand and competitors of Suntory Flowers also began to take steps to breed *Mandevilla* plants.

The following Patent Document 10 (assignee: Syngenta Participations AG) describes a new variety known as *Mandevilla sanderi* (Hems1.) Woodson 'Fisrix Pinka', obtained by crossing maternal plants in the form of the varieties 'Sundaville'™ Red and 'Moulin Rouge', which are supplied in France and are identical to the early blooming type "Crimson" described in Patent Document 3, with a paternal plant in the form of a variety supplied as 'My Fair Lady'™ referred to as 'Helle' described in Patent Document 1.

Patent Documents 11 to 13 (assignees: Floraquest Pty. Ltd. and Protected Plant Promotion Australia Pty. Ltd.) describe a novel variety known as *Mandevilla hybrida* 'Ginger', which was obtained by crossing a material plant in the form of a *Mandevilla hybrida* identified by the code number X02.5, and a paternal plant in the form of early blooming "Crimson" (*Mandevilla hybrida* 'Sunmandecrim') described in Patent Document 3.

PRIOR ART DOCUMENTS

Patent Documents

[Patent Document 1] U.S. Plant Patent No. 9117
[Patent Document 2] U.S. Plant Patent No. 11556
[Patent Document 3] U.S. Plant Patent No. 15539
[Patent Document 4] U.S. Plant Patent No. 15202
[Patent Document 5] U.S. Plant Patent No. 16449
[Patent Document 6] U.S. Plant Patent No. 16363
[Patent Document 7] U.S. Plant Patent No. 17736
[Patent Document 8] U.S. Plant Patent No. 18578
[Patent Document 9] U.S. Plant Patent No. 19649
[Patent Document 10] U.S. Plant Patent No. 20644
[Patent Document 11] U.S. Plant Patent No. 20776
[Patent Document 12] U.S. Plant Patent No. 20777
[Patent Document 13] U.S. Plant Patent No. 20919
[Patent Document 14] U.S. Plant Patent No. 20542
[Patent Document 15] U.S. Plant Patent No. 19399

Non-Patent Documents

[Non-Patent Document 1] The New York Botanical Garden Illustrated Encyclopedia of Horticulture, Vol. 6, p. 2129-2130, Garland Publishing, Inc. (1981)
[Non-Patent Document 2] Mabberley's Plant Book, Third Edition, p. 520, Cambridge University Press (2008)

DISCLOSURE OF THE INVENTION

Problems to be Solved by the Invention

Commercially available varieties of *Mandevilla* genus plants previously only consisted of varieties having white, pink or red flower color. Although there are wild species that have yellow flower color and a variety having yellow color (Opale Citrine) has been marketed in recent years, since these are unable to be crossed with varieties having white, pink or red flower color, hybrids having varieties having yellow flower color as hybrid parents have yet to be produced. Consequently, expression of new colors obtained by crossing varieties having yellow flower color with varieties having conventional white to pink to red flower color (flower color having an a* value of 0 to 60 and b* value of 0 to 40 in the CIE L*a*b color system) was unable to be realized. An object of the present invention is to provide a novel *Mandevilla* genus plant having a novel flower color tone that has been unable to be previously produced.

Means for Solving the Problems

When the inventors of the present invention recently acquired a strain 09M111-1 having novel color tone among seedlings obtained by crossing red varieties with white varieties and analyzing the pigment of the petals, they were found to have a trace amount of a unique carotenoid pigment. The inventors of the present invention surprisingly succeeded in producing a hybrid plant having a novel tone of flower color that was unable to be previously produced following the acquisition of hybrid seeds when a *Mandevilla* genus plant having this unique carotenoid pigment was crossed with a variety of *Mandevilla* genus plant having white, pink or red flower color.

More specifically, the present invention is as indicated below.

[1] A *Mandevilla* genus plant containing at least one or more types of carotenoid pigment in the petals thereof; wherein, the carotenoid pigment is neoxanthin or a derivative thereof.

[2] The *Mandevilla* genus plant described in 1, wherein the carotenoid pigment is neoxanthin dimyristate, neoxanthin 3-O-myristate-3'-O-palmitate, neoxanthin 3-O-palmitate-3'-O-myristate, neoxanthin dipalmitate or a combination thereof.

[3] A *Mandevilla* genus plant containing at least one or more types of carotenoid pigment in the petals thereof wherein, the carotenoid pigment is a compound corresponding to peak A, peak C or peak D in the chromatographs shown in FIGS. 1, 2 and 5.

[4] A *Mandevilla* genus plant containing neoxanthin synthase in the petals thereof.

[5] The *Mandevilla* genus plant described in any of 1 to 4, having flower color having an a* value of −10 to 70 and a b* value of 0 to 80 in the CIE L*a*b color system.

[6] The *Mandevilla* genus plant described in 5, having flower color other than flower color having an a* value of 0 to 30 and a b* value of 0 to 5 in the CIE L*a*b color system.

[7] The *Mandevilla* genus plant described in any of 1 to 4, having flower color having an a* value of −5 to 20 and a b* value of 3 to 70, or having an a* value of 50 to 70 and a b* value of 5 to 70 in the CIE L*a*b color system.

[8] The *Mandevilla* genus plant described in any of 1 to 7, containing 0.02 mg or more of anthocyanin pigment per 1 g of fresh petals.

[9] The *Mandevilla* genus plant described in 8, wherein the anthocyanin pigment is cyanidin.

[10] A *Mandevilla* genus plant designated as 09M111-1 (accession number: FERM BP-22298).

[11] A progeny of the *Mandevilla* genus plant described in any of 1 to 10.

[12] A vegetative propagant, portion of a plant body, tissue or cells of the *Mandevilla* genus plant according to any of 1 to 10 or a progeny thereof.

[13] A cut flower or a processed plant product produced from that cut flower of the *Mandevilla* genus plant described in any of 1 to 10 or a progeny thereof.

[14] A method for selecting a parent *Mandevilla* genus plant containing carotenoid pigment in the petals thereof and capable of being crossed with a *Mandevilla* genus plant having white to pink to red color (flower color having an a* value of 0 to 60 and a b* value of 0 to 40 in the CIE L*a*b color system), comprising:

selecting a candidate *Mandevilla* genus plant as a parent *Mandevilla* genus plant in the case carotenoid pigment in the form of neoxanthin or a derivative thereof is present in the petals thereof.

[15] The method described in [14], wherein the carotenoid pigment is neoxanthin dimyristate, neoxanthin 3-O-myristate-3'-O-palmitate, neoxanthin 3-O-palmitate-3'-O-myristate, neoxanthin dipalmitate or a combination thereof.

[16] A method for selecting a parent *Mandevilla* genus plant containing carotenoid pigment in the petals thereof and capable of being crossed with a *Mandevilla* genus plant having white to pink to red color (flower color having an a* value of 0 to 60 and a b* value of 0 to 40 in the CIE L*a*b color system), comprising:

selecting a candidate *Mandevilla* genus plant as a parent *Mandevilla* genus plant in the case a compound corresponding to peak A, peak C or peak D in the chromatographs shown in FIGS. 1, 2 and 5 is present in the petals thereof.

[17] A method for selecting a parent *Mandevilla* genus plant capable of being crossed with a *Mandevilla* genus plant having white to pink to red petals (flower color having an a* value of 0 to 60 and a b* value of 0 to 40 in the CIE L*a*b color system), comprising:

selecting a candidate *Mandevilla* genus plant as a parent *Mandevilla* genus plant in the case neoxanthin synthase is present in the petals thereof.

[18] The method described in any of 14 to 17, wherein the color tone of petals of a candidate *Mandevilla* genus plant in the CIE L*a*b* color system is measured, and the candidate *Mandevilla* genus plant is selected as a parent *Mandevilla* genus plant in the case the a* value is −10 to 70 and the b* value is 0 to 80.

[19] The method described in 18, wherein a candidate *Mandevilla* genus plant is excluded from selection of a parent *Mandevilla* genus plant in the case the a* value is 0 to 30 and the b* value is 0 to 5.

[20] The method described in any of 14 to 17, wherein the color tone of petals of a candidate *Mandevilla* genus plant in the CIE L*a*b* color system is measured, and the candidate *Mandevilla* genus plant is selected as a parent *Mandevilla* genus plant in the case the a* value is −5 to 20 and the b* value is 3 to 70, or the a* value is 50 to 70 and the b* value is 5 to 70.

[21] The method described in any of 14 to 20, wherein the amount of anthocyanin in the petals of a candidate *Mandevilla* genus plant is measured, and the candidate *Mandevilla* genus plant is selected as a parent *Mandevilla* genus plant in the case of containing 0.02 mg or more of anthocyanin pigment per 1 g of fresh petals.

[22] The method described in 21, wherein the anthocyanin pigment is cyanidin.

[23] The method described in any of 14 to 22, wherein a *Mandevilla* genus plant designated as 09M111-1 (accession number: FERM BP-22298) is selected as a parent *Mandevilla* genus plant.

[24] A method for producing a *Mandevilla* genus plant having petals of a flower color having an a* value of −10 to 70 and b* value of 0 to 80 in the CIE L*a*b* color system (such as yellow to apricot to orange color, and particularly ivory, light yellow, yellow, apricot, orange-pink, orange-red or orange), comprising:
a step for selecting a first *Mandevilla* genus parent plant according to the method described in any of 14 to 23, and
a step for crossing the selected first *Mandevilla* genus parent plant with a second *Mandevilla* genus parent plant.

[25] The method described in 24, wherein the second *Mandevilla* genus parent plant has petals having white to pink to red color (flower color having an a* value of 0 to 60 and b* value of 0 to 40 in the CIE L*a*b* color system).

Effects of the Invention

According to the present invention, a novel *Mandevilla* genus plant having petals having a novel color tone that had not previously existed can be produced by crossing a variety of *Mandevilla* genus plant having white to pink to red flower color with a variety having yellow pigment for which crossbreeding was previously not possible.

BEST MODE FOR CARRYING OUT THE INVENTION

Figure 1:
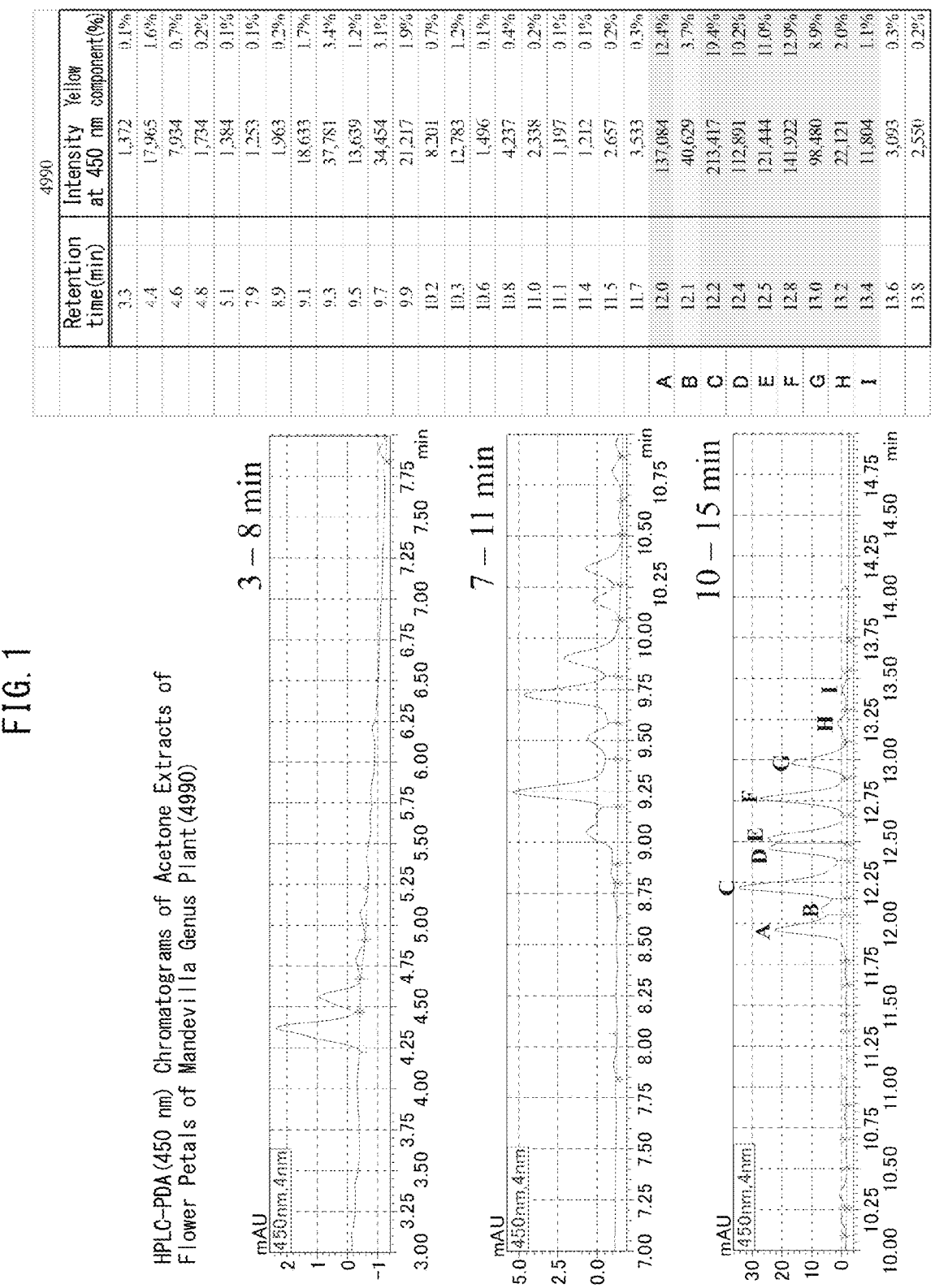
FIG. 1 is an HPLC-PDA (450 nm) chromatogram of an acetone extract of the petals of a *Mandevilla* genus plant (4990) of the present invention.
Figure 2:
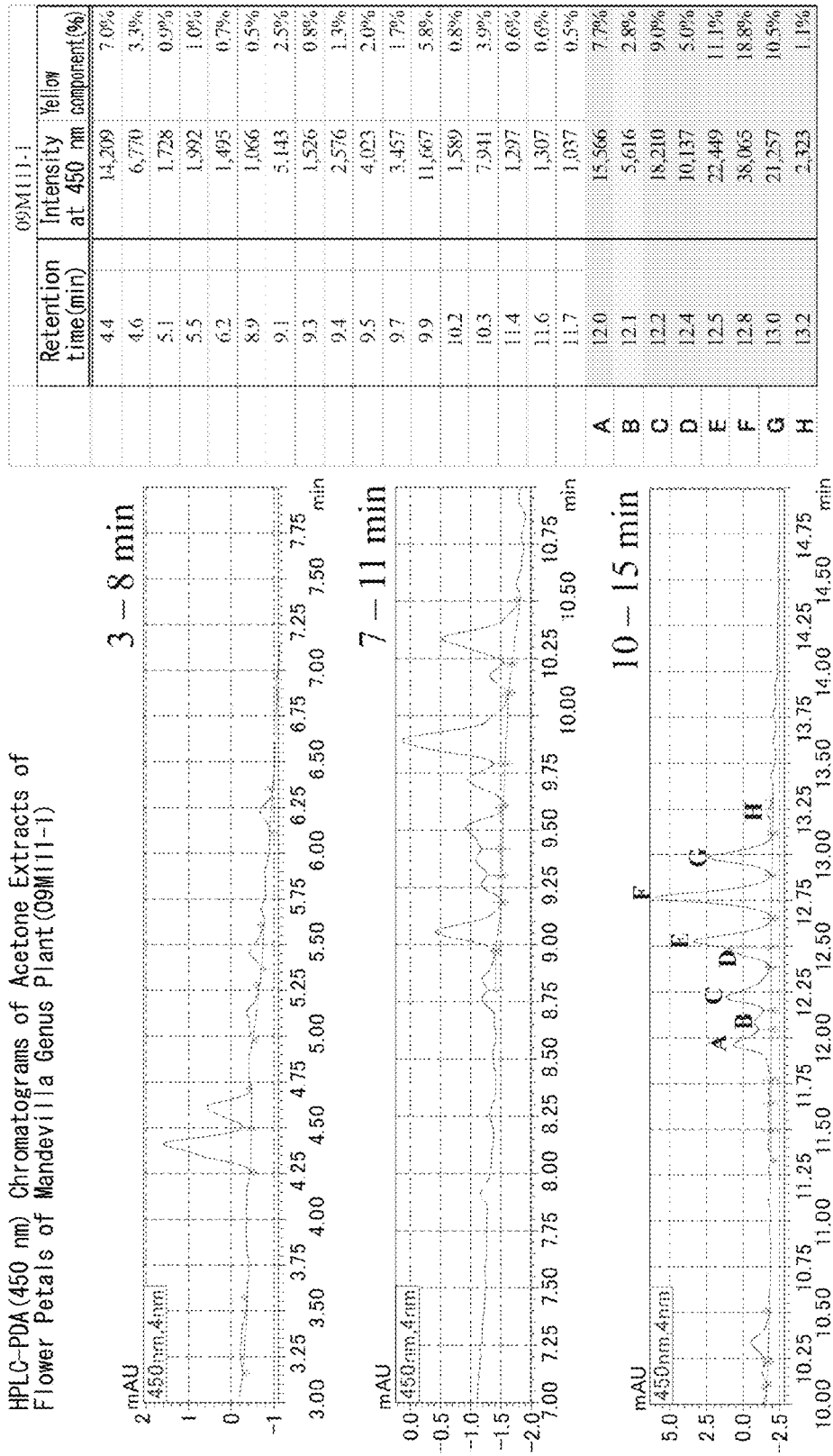
FIG. 2 is an HPLC-PDA (450 nm) chromatogram of an acetone extract of the petals of a *Mandevilla* genus plant (09M111-1) of the present invention.
Figure 5:
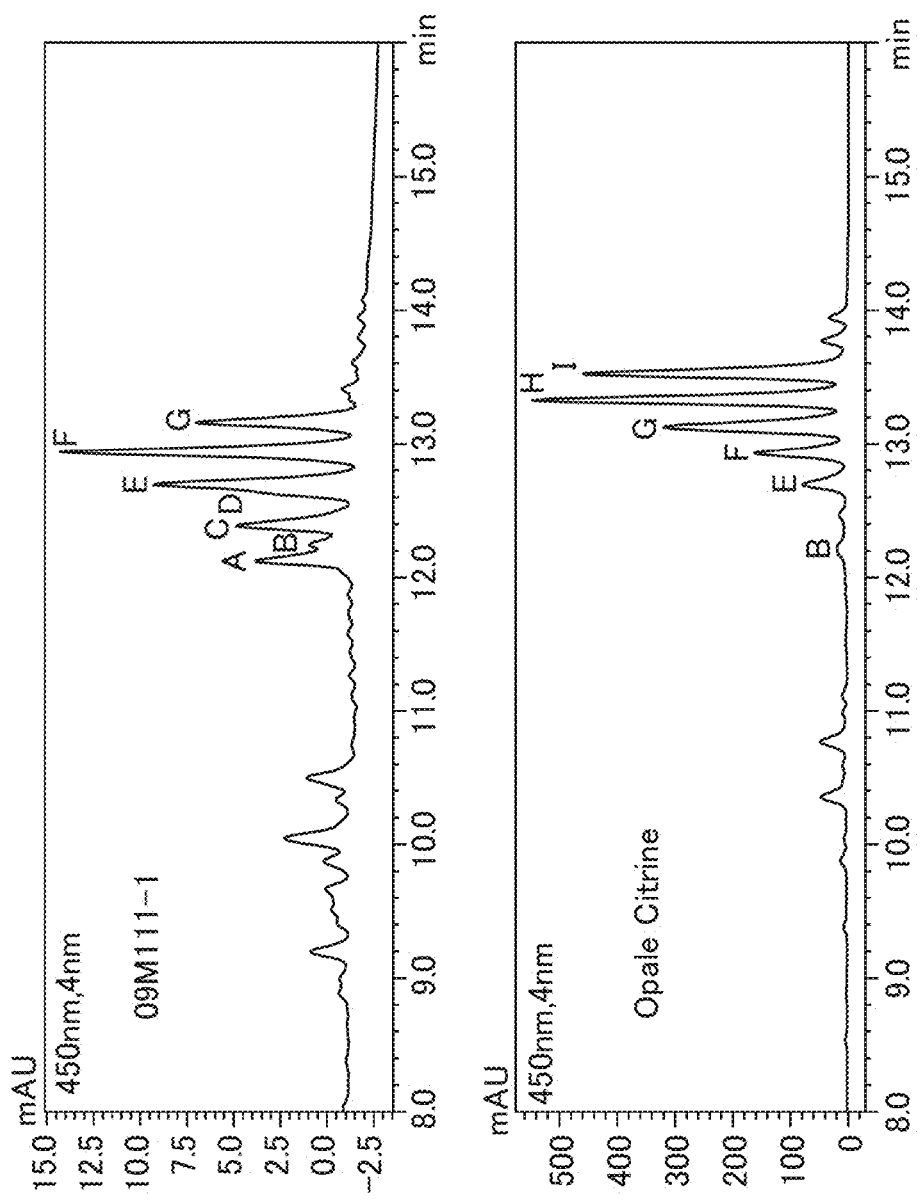
FIG. 5 indicates HPLC-PDA (450 nm) chromatograms of a *Mandevilla* genus plant of the present invention (09M111-1) and an existing *Mandevilla* genus plant (Opale Citrine).

A first aspect of the present invention provides a *Mandevilla* genus plant containing at least one or more types of carotenoid pigment in the petals thereof, wherein the carotenoid pigment is a compound corresponding to peak A, peak C or peak D in the chromatogram shown in FIGS. 1, 2 and 5.

Carotenoid pigment refers to a group of natural pigments exhibiting yellow color, orange color or red color and the like, and an extremely large number of types of carotenoids have heretofore been isolated and identified from animals and plants. Carotenoids are typically known to be a type of terpenoid classified as tetraterpenes that have a basic skeleton represented by the chemical formula $C_{40}H_{56}$ and are composed by the bonding of 8 isoprene units. Carotenoids exhibit different absorption spectra having peaks between 400 nm and 500 nm due to the presence of conjugated double bonds in the molecular structure thereof, and as a result, exhibit color ranging from yellow to orange to red.

As a result of conducting extensive studies, the inventors of the present invention further succeeded in identifying compounds corresponding to these peaks, and obtained the surprising finding that compounds corresponding to these peaks have the basic skeleton of neoxanthin.

Thus, another aspect of the present invention provides a *Mandevilla* genus plant containing at least one or more types of carotenoid pigment in the petals thereof, wherein the carotenoid pigment is neoxanthin or a derivative thereof.

Neoxanthin is an intermediate in the biosynthesis of the plant hormone, abscisic acid, which is synthesized from violaxanthin by neoxanthin synthase and has the chemical structure indicated below.

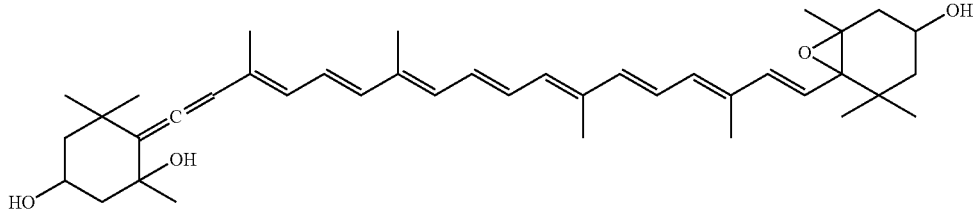 [SMILES: C\C(C=C=C1C(C)(C)CC(O)CC1(C)O)=C/C=C/C(C)=C/C=C/C=C(C)/C=C/C=C(C)/C=C/C12OC1(C)CC(O)CC2(C)C]

Although neoxanthin and violaxanthin are types of yellow pigments derived from carotenoids in the form of xanthophylls, as is also indicated in the subsequent examples, although violaxanthin derivatives are present in existing *Mandevilla* genus plants (Opale Citrine), it is a very unexpected thing that neoxanthin derivatives is contained only in the *Mandevilla* genus plant of the present invention (09M111-1).

Examples of neoxanthin derivatives include fatty acid esters of neoxanthin. Examples of fatty acids that form these fatty acid esters include, but are not limited to, butyric acid, valeric acid, caproic acid, enanthic acid, caprylic acid, pelargonic acid, capric acid, lauric acid, myristic acid, pentadecyl acid, palmitic acid, palmitoleic acid, margaric acid, stearic acid, oleic acid, vaccenic acid, linoleic acid, linolenic acid, eleostearic acid, arachidic acid, mead acid, arachidonic acid, behenic acid, lignoceric acid, nervonic acid, cerotic acid, montanic acid and melissic acid. The neoxanthin derivative is preferably a neoxanthin diester having fatty acids bound to each of the hydroxyl groups at the 3 position and 3' position of neoxanthin, and is particularly preferably neoxanthin dimyristate, neoxanthin 3-O-myristate-3'-O-palmitate, neoxanthin 3-O-palmitate-3'-O-myristate or neoxanthin dipalmitate.

In addition, since the *Mandevilla* genus plant of the present invention contains neoxanthin or a derivative thereof as carotenoid pigment in the petals thereof, it is thought to contain neoxanthin synthase as an enzyme involved in biosynthesis. Neoxanthin synthase is an enzyme that converts violaxanthin to neoxanthin by introducing an allene group therein and forms neoxanthin by using violaxanthin as a substrate. Thus, another aspect of the present invention provides a *Mandevilla* genus plant containing neoxanthin synthase in the petals thereof.

The *Mandevilla* genus plant of the present invention may have flower color having an a* value of −10 to 70 and a b* value of 0 to 80 in the CIE L*a*b* color system. In this case, the *Mandevilla* genus plant of the present invention preferably has flower color other than flower color having an a* value of 0 to 30 and b* value of 0 to 5. Optimally, the *Mandevilla* genus plant has flower color having an a* value of −5 to 20 and b* value of 3 to 70, or flower color having an a* value of 50 to 70 and b* value of 5 to 70.

The CIE L*a*b* color system is a color system standardized by the International Commission on Illumination (CIE) that is widely known to be a notation for representing color tone and is also referred to as the CIE1976 (L*a*b*) color system. In the L*a*b* color system, lightness is represented by L*, and chromaticity indicating hue and saturation are represented by a* and b*. a* and b* respectively indicate color directions, with a* representing the red direction, −a* representing the green direction, b* representing the yellow direction and −b* representing the blue direction. Each of the values of L*, a* and b* can be obtained from the tristimulus values of X, Y and Z using the equations indicated below.

$$L^* = 116(Y/Y_0)^{1/3} - 16$$

$$a^* = 500[(X/X_0)^{1/3} - (Y/Y_0)^{1/3}]$$

$$b^* = 200[(Y/Y_0)^{1/3} - (Z/Z_0)^{1/3}]$$

However, the values of $X/X_0$, $Y/Y_0$ and $Z/Z_0$ are greater than 0.008856, and in the equations, $X_0$, $Y_0$ and $Z_0$ represent the tristimulus values of a standard light source.

Furthermore, the color difference ΔE between two different colors in the form of $L^*_1$, $a^*_1$ and $b^*_1$ and $L^*_2$, $a^*_2$ and $b^*_2$ can be determined from the equation indicated below.

$$\Delta E = \sqrt{(L^*_2 - L^*_1)^2 + (a^*_2 - a^*_1)^2 + (b^*_2 - b^*_1)^2}$$

Analysis of colors with the CIE L*a*b* color system can be easily carried out using an integrating sphere-type spectrocolorimeter, and a commercially available spectrophotometer (such as the CM-2002, Konica Minolta) can be used.

In addition, the *Mandevilla* genus plant of the present invention may contain 0.02 mg or more, preferably 0.05 mg or more and optimally 0.07 mg of anthocyanin per 1 g of fresh petals.

Anthocyanin pigment is contained in plants and is known to exhibit red, blue and violet flower color. Anthocyanin pigment is classified into three types consisting of pelargonidin, cyanidin and delphinidin depending on the number of hydroxyl groups of the B ring of an aglycone site in the form of an anthocyanidin site. The chromophore is the aglycone moiety, with pelargonidin known to exhibit vivid red color, cyanidin red-violet color and delphinidin violet-red color. The main anthocyanidin pigment contained in the *Mandevilla* genus plant of the present invention is cyanidin.

Although there are no particular limitations on the *Mandevilla* genus plant of the present invention provided it satisfies the aforementioned conditions, preferable examples thereof include 09M111-1 and hybrid plants having 09M111-1 as a parent plant thereof. A cultured seedling of 09M111-1 was deposited based on the Budapest Treaty (accession number: FERM BP-22298) at the International Patent Organism Depository (NITE-IPOD) of the National Institute of Technology and Evaluation (NITE) (#120, 2-5-8 Kazusakamatari, Kisarazu-shi, Chiba, Japan) on Oct. 9, 2015.

The present invention includes progeny of the aforementioned *Mandevilla* genus plant. These progeny preferably have the same desirable traits as the aforementioned *Mandevilla* genus plant. The present invention includes a vegetative propagant, portion of a plant body (such as a flower, stem, branch, leaf or root), tissue or cells of the aforementioned *Mandevilla* genus plant or progeny thereof. Moreover, the present invention includes a cut flower or a processed plant product produced from that cut flower of the aforementioned *Mandevilla* genus plant or progeny thereof.

A second aspect of the present invention provides a method for selecting a parent *Mandevilla* genus plant containing carotenoid pigment in the petals thereof and capable of being crossed with a *Mandevilla* genus plant having white to pink to red petals, comprising:

extracting carotenoid pigment from the petals of a candidate *Mandevilla* genus plant and selecting a candidate *Mandevilla* genus plant as a parent *Mandevilla* genus plant in the case carotenoid pigment in the form of a compound corresponding to peak A, peak C or peak D in the chromatographs of FIGS. 1, 2 and 5 (and more specifically, the aforementioned neoxanthin or a derivative thereof), or neoxanthin synthase, is present in the carotenoid pigment extract. The presence of neoxanthin synthase can be confirmed by a method that is customary among persons with ordinary skill in the art such as identification of neoxanthin synthase gene by PCR or direct identification of neoxanthin synthase by mass spectrometry.

*Mandevilla* genus plants have a unique flower structure that makes artificial crossbreeding by artificial pollination technically difficult. Despite the existence of roughly more than 130 original species, only just over 10 species are used horticulturally. Consequently, although wild types having yellow flower color exist, hybrid *Mandevilla* genus plants obtained by using conventional varieties having yellow flower color as hybrid parents have yet to be produced, and the expression of novel colors through crossbreeding between *Mandevilla* varieties having yellow flower color and *Mandevilla* varieties having conventional white to pink to red flower color has been unable to be realized. However, according to the method of the present invention, a *Mandevilla* genus plant having a carotenoid-based flower color that is capable of being crossed with a *Mandevilla* genus plant having white to pink to red petals can be easily selected for use as a parent plant.

In the aforementioned method for selecting a parent *Mandevilla* genus plant of the present invention, in the case of having measured color tone of the petals of a candidate *Mandevilla* genus plant according to the CIE L*a*b* color system and the a* value is −10 to 70 and the b* value is 0 to 80, that candidate *Mandevilla* genus plant may be selected as a parent *Mandevilla* genus plant. In this case, a candidate *Mandevilla* genus plant is preferably excluded from selection of a parent *Mandevilla* genus plant in the case the a* value is 0 to 30 and the b* value is 0 to 5. Optimally, a candidate *Mandevilla* genus plant is selected for use as a parent *Mandevilla* genus plant in the case of having measured color tone of the petals of the candidate *Mandevilla* genus plant according to the CIE L*a*b* color system and the a* value is −5 to 20 and the b* value is 3 to 70 or the a* value is 50 to 70 and the b* value is 5 to 70.

In addition, in the aforementioned method for selecting a parent *Mandevilla* genus plant of the present invention, in the case of having measured the amount of anthocyanin pigment in the petals of a candidate *Mandevilla* genus plant and the petals contain 0.02 mg or more, preferably 0.05 mg or more and optimally 0.07 mg or more of anthocyanin pigment per 1 g of fresh petals, that candidate *Mandevilla* genus plant may be selected as a parent *Mandevilla* genus plant. The anthocyanin pigment is preferably cyanidin.

Although there are no particular limitations on the parent *Mandevilla* genus plant provided it is obtained according to the aforementioned selection method of the present invention, preferable examples thereof include 09M111-1 and hybrid plants obtained by using 09M111-1 as a parent plant thereof.

Moreover, the present invention includes a method for producing a *Mandevilla* genus plant containing carotenoid pigment in the petals thereof, comprising a step for selecting a first *Mandevilla* genus parent plant according to the aforementioned method for selecting a parent *Mandevilla* genus plant of the present invention, and a step for crossing the first *Mandevilla* genus parent plant with a second *Mandevilla* genus parent plant.

Although there are no particular limitations on the second *Mandevilla* genus parent plant provided it can be crossed with the first *Mandevilla* genus parent plant, it is preferably a *Mandevilla* genus plant having white to pink to red petals. Examples thereof include large-blooming type "Crimson King" (*Mandevilla hybrida* 'Sunmandecrikin') large-blooming type "White" (*Mandevilla amabilis×boliviensis* 'Sunmandeho') and vine-blooming type "Tropical Peach" (*Mandevilla hybrida* 'Sunmandetomi').

Crossbreeding is carried out by open pollination or hand pollination. Since the maturation period of the seeds of *Mandevilla* genus plants is about six months, which is extremely long in comparison with ordinary plants, it is important to maintain the plants without cutting the flower styles for a period of time until the seeds have matured to a certain degree after crossing.

According to the present invention, a novel *Mandevilla* genus plant can be produced that has a novel color tone unable to be previously produced, and more particularly, a novel *Mandevilla* genus plant having yellow to apricot to orange flower color (such ivory, light yellow, yellow, apricot, orange-pink, orange-red or orange flower color).

Examples

1. Production of *Mandevilla* Genus Plant

Crossbreeding was carried out in a greenhouse of the Suntory Flowers Global Breeding and Resource Center in May 2009 using as crossing materials a maternal plant in the form of variety MR-7 having red flower color retained by Suntory Flowers Ltd. (which subsequently withered) and a paternal plant in the form of Sunparasol Clear White (registered variety name: Sunparacoho) having white flower color. The hybrid seeds were harvested in November 2009. The seeds were planted in a greenhouse in November 2009. 100 seedlings demonstrating favorable growth were selected from among the seedlings that germinated, potted in 9 cm pots and grown in a greenhouse controlled to nighttime minimum temperature of 16° C. followed by transplanting to 18 cm pots in May 2010 and subjecting to a growing test in an outdoor field of the Suntory Flowers Global Breeding and Resource Center. The flowers that bloomed were selecting using flower color novelty, viability and heat tolerance as indicators in September 2010 to select 09M111-1 having apricot flower color (L*=81.8, a*=11.7, b*=28.3).

09M111-1 was allowed to undergo inbred crossing in a greenhouse of the Suntory Flowers Global Breeding and Resource Center in October 2010. The inbred seeds were harvested in May 2011. The inbred seeds were planted in a greenhouse in November 2011. 100 seedlings demonstrating favorable growth were selected from among the seedlings that germinated, potted in 9 cm pots, and grown in a greenhouse controlled to nighttime minimum temperature of 16° C. followed by transplanting to 18 cm pots in May 2012 and subjecting to a growing test in an outdoor field of the Suntory Flowers Ltd. Individual 09M111-1self-1 plants that exhibited an intense yellowish color were selected from the flowers that bloomed using flower color as an indicator in September 2012. Subsequently, crossbreeding using 09M111-1 for the maternal plant and 09M111-1self-1 for the paternal plant was carried out in May 2013 in a greenhouse of the Suntory Flowers Global Breeding and Resource Center. The hybrid seeds were harvested in November 2013. The hybrid seeds were planted in November 2013. 100 seedlings demonstrating favorable growth were selected from among seedlings that germinated, potted in 9 cm pots, and grown in a greenhouse controlled to a nighttime minimum temperature of 16° C. followed by transplanting to 18 cm pots in May 2014 and subjecting to a growing test in an outdoor field of the Suntory Flowers Global Breeding and Resource Center. The flowers that bloomed were selected using flower color novelty, viability and heat tolerance as indicators in September 2014 to select #4990 having yellow flower color (L*=82.4, a*=8.6, b*=48.0).

09M111-1self-1 plants were arranged in close proximity to a plurality of red strains having high petal cyanidin contents and allowed to open-pollinate in an outdoor field of the Suntory Flowers Global Breeding and Resource Center in May 2013. Fruition seeds having 09M111-1self-1 as maternal plants thereof were harvested in November 2013. The seeds were planted in a greenhouse in November 2013. The hybrid seeds were planted in November 2013. 100 seedlings demonstrating favorable growth were selected from among seedlings that germinated, potted in 9 cm pots, and grown in a greenhouse controlled to a nighttime minimum temperature of 16° C. followed by transplanting to 18 cm pots and managing in an open field of Suntory Flowers Ltd. The flowers that bloomed were selected using flower color novelty, viability and heat tolerance as indicators in September 2014 to select #4891 having orange-red flower color (L*=36.2, a*=54.0, b*=41.4).

2. Analysis of Carotenoid Pigment

The contents of carotenoid pigment components present in the petals of *Mandevilla* genus plant varieties consisting of 4990, 09M111-1 and Opale Citrine were quantified in the manner described below.

Quantitative analyses were carried out using a high-performance liquid chromatography-photodiode array detection (HPLC-PDA) system capable of detecting with a photodiode array (PDA) detector enabling favorable analysis of yellow pigment.

The test liquids were prepared by weighing out 5 mg of dried petals subjected to freeze-drying treatment, adding 0.5 mL of acetone, and irradiating with ultrasonic waves for 20 minutes at 25° C. using an ultrasonic cleaner (As One, AS52GTU) to carry out a procedure for extracting the yellow pigment component. 0.3 mL of a supernatant of the HPLC-PDA test liquid into which the yellow pigment component had been extracted was filtered with a filter having a pore size of 0.45 μm (Nacalai Tesque, Cosmonice Filter S (solvent type).

The configuration of the high-performance liquid chromatography photodiode array detection (HPLC-PDA) system consisted of the use of the Nexera LC-30AD (Shimadzu) for the liquid feed unit LC pump, the Prominence SPD-M20A (Shimadzu) for the PDA detector, and the Develosil C30-UG-3 (2.0 mm×100 mm, Nomura Chemical) for the separation column. Delivery of the LC mobile phase consisted of using a mixture of methanol and water (80/20, vol/vol) for mobile phase A, using a mixture of t-butyl methyl ether, methanol and water (78/20/2, vol/vol/vol) for mobile phase B, changing the binary gradient from a mobile phase B concentration of 0% to 100% over the course of 15 minutes, and setting the flow rate to 0.4 mL/min. 10 μL of test liquid extracted from the petals were injected.

Optical absorbance was measured with the PDA detector over the range of 200 nm to 800 nm and particular attention was focused on the blue absorbance band from 440 nm to 490 nm, which is the complementary color of yellow. The absorbance of each peak obtained by LC-PDA at 450 nm was used for the quantitative values.

Figure 3:
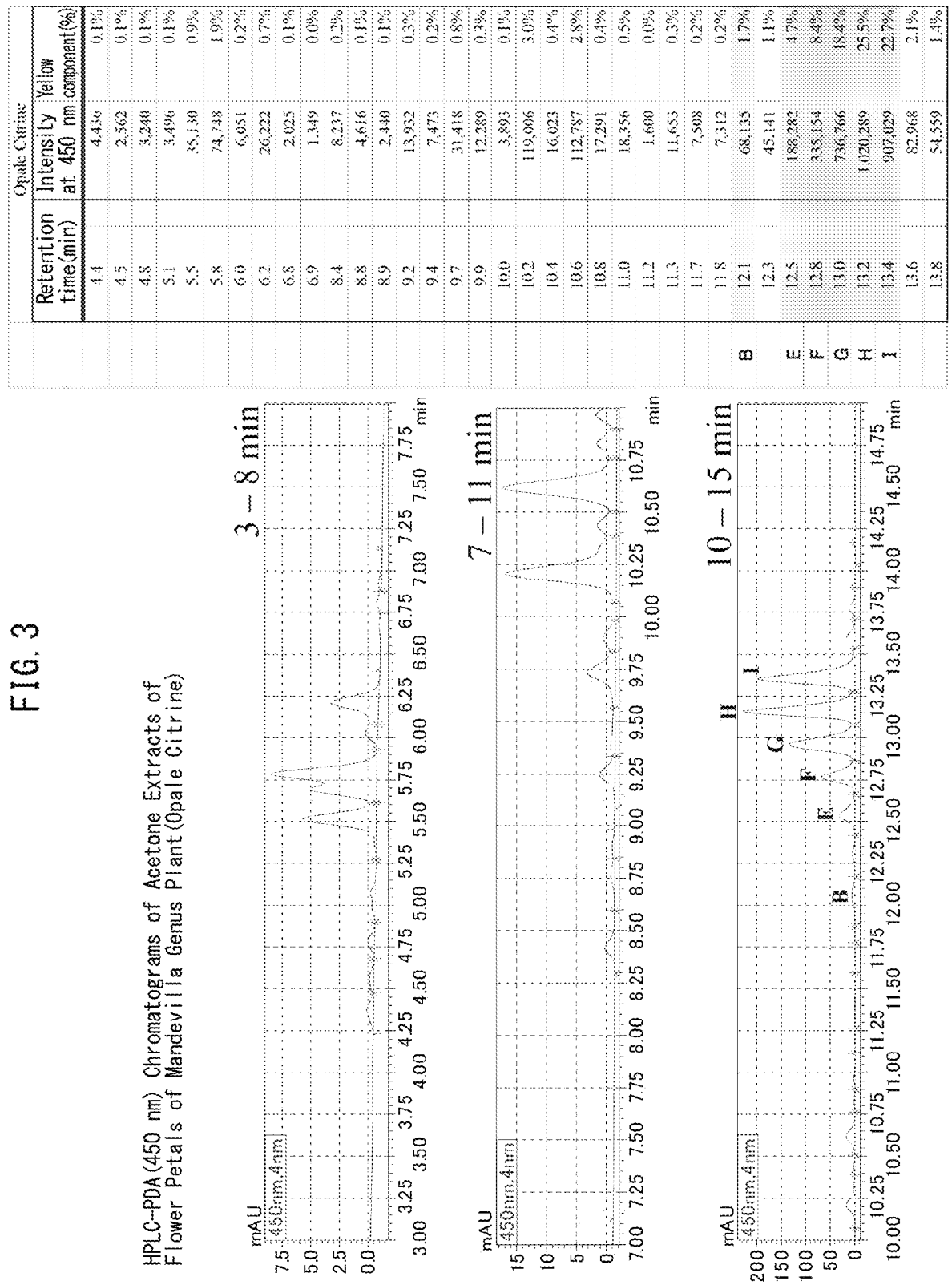
FIG. 3 is an HPLC-PDA (450 nm) chromatogram of an acetone extract of petals of a *Mandevilla* genus plant (Opale Citrine) of the prior art.

The results are shown in FIGS. 1 to 3.

3. Analysis of Flavonoids

*Mandevilla* flower petals were collected and freeze-dried followed by extracting flavonoids from the petals with 50% acetonitrile aqueous (v/v) containing 0.1% trifluoroacetic acid (TFA). After dispensing 0.2 ml of the extract and drying, the extract was dissolved in 0.2 ml of HCl followed by treating for 20 minutes at 100° C. to obtain anthocyanidin. 0.2 ml of the resulting anthocyanidin was extracted with 1-pentanol followed by subjecting to HPLC analysis. Analysis was carried out using an ODS-A312 column (15 cm×6 mm, YMC) with an isocratic solvent (mixture of AcOH, MeOH and $H_2O$, 15/20/65, v/v/v) at a flow rate of 1 ml/min.

Next, 200 μl of the flower petal extract prepared in the manner described above were dispensed and dried followed by dissolving in 0.1 M potassium phosphate buffer containing 6 units of β-glucosidase (Sigma, St. Louis, MO., USA) and 1 unit of naringinase (Sigma) and treating for 16 hours at 30° C. to obtain flavonol by hydrolysis. 200 μl of 90% (v/v) acetonitrile containing 0.1% TFA were then added thereto to stop the reaction followed by subjecting to HPLC analysis. Analysis was carried out with a Shim-pack FC-ODS column (15 cm×4.6 mm, Shimadzu) at a flow rate of 0.6 ml/min using a solvent A (mixture of $H_2O$ and TFA, 99.9/0.1, v/v) and solvent B (mixture of $H_2O$, acetonitrile and TFA, 9.9/90/0.1, v/v/v). The conditions for gradient analysis were as indicated below.

0 minutes: Solvent B 20%
0-10 minutes: Solvent B 70%
10-16 minutes: Solvent B 70%
16-17 minutes: Solvent B 20%
17-28 minutes: Solvent B 20%

The anthocyanidin and flavonol were detected at optical absorbance of 250 nm to 400 nm using a photodiode array detector (SPD-M20A, Shimadzu).

The results are shown in the table below.

TABLE 1

| | | Anthocyanidin | | |
| | | Delphinidin | Cyanidin | Pelargonidin |
| | | | mg/g fresh petals | |
|---|---|---|---|---|
| Mandevilla Opale Citrine | Yellow | 0.0000 | 0.0157 | 0.0000 |
| Mandevilla 4990 | Cream yellow | 0.0000 | 0.0785 | 0.0000 |
| Mandevilla 09M111-1 | Apricot | 0.0000 | 0.1506 | 0.0000 |
| Mandevilla 104 | White | 0.0000 | 0.0826 | 0.0046 |
| Mandevilla 173 | Red | 0.0000 | 2.6051 | 0.0437 |

4. Colorimetry

The colorimetric values of the flat open portion of the corolla were measured using a spectrophotometer (CM2022, Minolta) for varieties produced in the present invention along with existing varieties using D65 illumination. The measured values were converted to numerical values in accordance with the CIE L*a*b* color system (C.I.E., 1986; Gonnet & Hieu, 1992; McLaren, 1976). Three individual flowers were measured for each variety and the average value thereof was taken to be the representative value of each flower. Distribution of flower color was represented two-dimensionally with a scatter diagram using chromaticity values a* and b* for the coordinate axes to confirm distribution for each color group.

Figure 4:
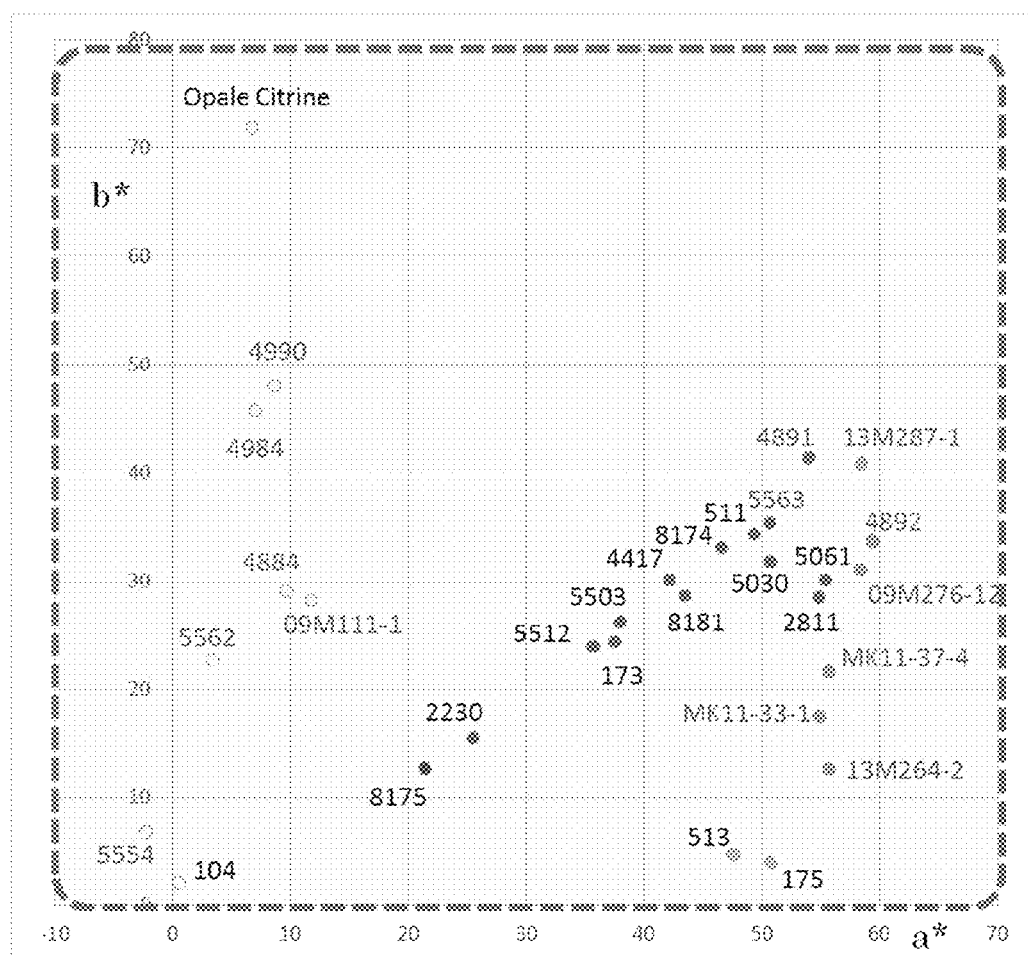
FIG. 4 indicates spectrocolorimetric data of the flower color of a *Mandevilla* genus plant variety of the present invention and an existing *Mandevilla* genus plant variety.

The results are shown in FIG. 4.

5. Analysis of Yellow Pigment

Characteristic yellow pigment components were analyzed by comparing 09M111-1 and Opale Citrine.

Structural analysis of yellow pigment components characterizing flower petals in the present invention was carried out based on (i) absorption spectrum as determined with a high-performance liquid chromatography (HPLC) photodiode array (PDA) detector, (ii) proton nuclear magnetic resonance spectrum ($^1$H-NMR), and (iii) high-resolution mass spectrum (HRMS).

(i) Detection of Yellow Pigment Components with High-Performance Liquid Chromatography (HPLC) Photodiode Array (PDA) Detector The absorption spectra of several types of contained yellow pigment components were acquired with a high-performance liquid chromatography (HPLC) photodiode array (PDA) detector capable of acquiring separation and ultraviolet-visible spectrophotometric data online. PDA requires the obtaining of absorption spectra over a range of 400 nm to 500 nm representing yellow colors. Actual acquisition of PDA data was carried out over the range of 200 nm to 800 nm.

Test liquids were prepared by weighing out 5.0 mg of each dry flower in a glass vial after undergoing freeze-drying treatment followed by the addition of 0.5 mL of extraction solvent in the form of acetone and irradiating with ultrasonic waves for 20 minutes at a set temperature of 25° C. with an ultrasonic cleaner (As One, AS52GTU) to extract yellow pigment components. 0.3 mL of supernatant of the test liquids into which the yellow pigment components had been extracted were filtered using a filter having a pore size of 0.45 μm (Nacalai Tesque, Cosmonice Filter S (solvent type)).

HPLC conditions consisted of the use of a reverse phase column chemically modified with octadecyl groups (C18) and triacontyl groups (C30) for the separation column, and the use of a mixed solvent of tert-butyl methyl ether, methanol and water for the mobile phase so as not to impair the absorption spectrum over the range of 300 nm to 600 nm.

The configuration of the HPLC-PDA system consisted of the use of the Nexera LC-30AD (Shimadzu) for the liquid feed unit LC pump, the Prominence SPD-M20A (Shimadzu) for the PDA detector, and the Develosil C30-UG-3 (2.0 mm×100 mm, Nomura Chemical) for the separation column. Delivery of the LC mobile phase consisted of using a mixture of methanol and water (80/20, vol/vol) for mobile phase A, using a mixture of t-butyl methyl ether, methanol and water (78/20/2, vol/vol/vol) for mobile phase B, changing the binary gradient from a mobile phase B concentration of 0% to 100% over the course of 15 minutes, and setting the flow rate to 0.4 mL/min. 10 μL of test liquid extracted from the petals were injected for analysis.

FIG. 5 indicates PDA (450 nm) chromatograms of 09M111-1 and Opale Citrine.

Figure 6:
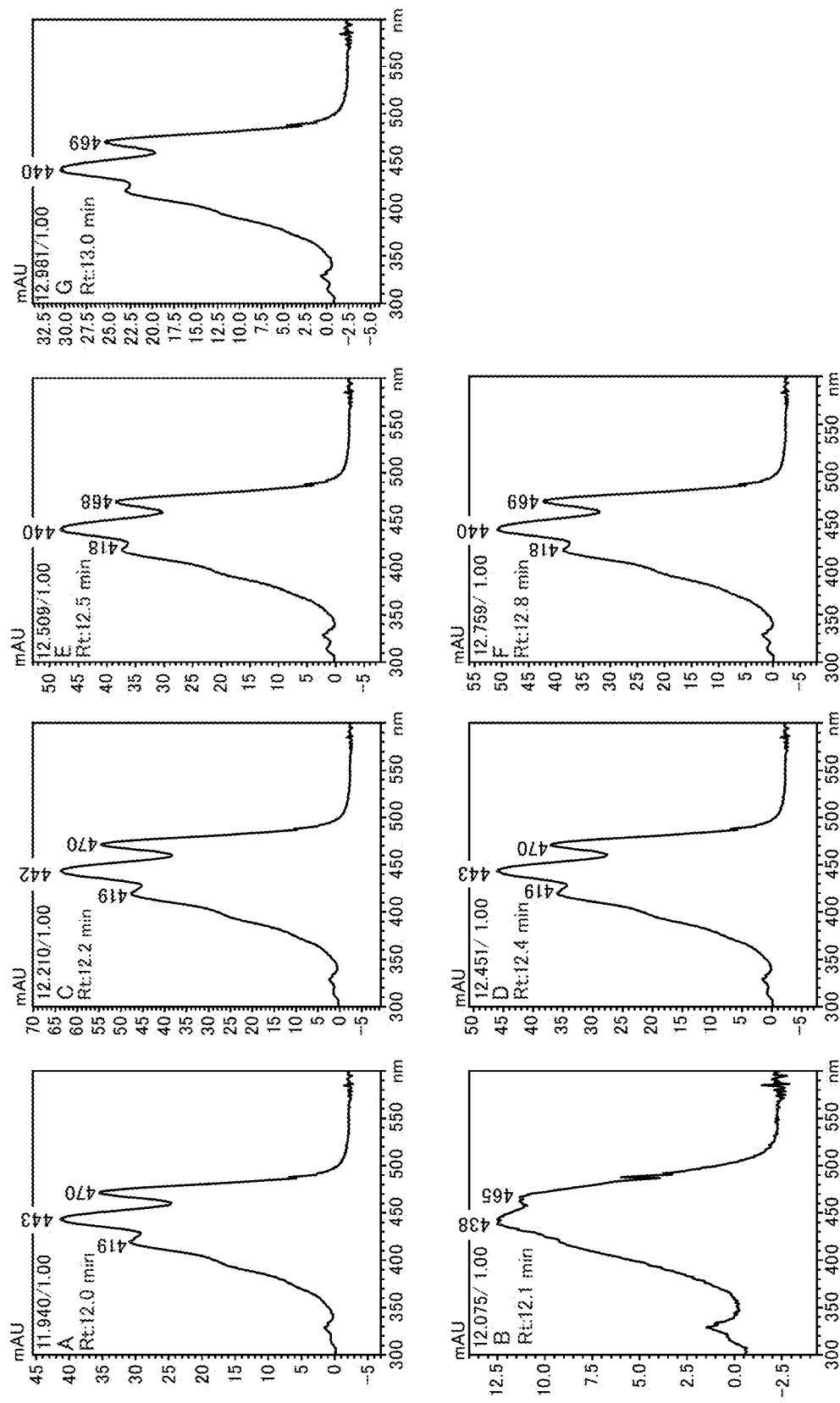
FIG. 6 indicates excerpted absorption spectra of peaks observed in an HPLC-PDA (450 nm) chromatogram of a *Mandevilla* genus plant of the present invention (09M111-1).

Upon comparison of the spectra, although peak A (retention time: 12.0 min), peak C (retention time: 12.2 min) and peak D (retention time: 12.4 min) were observed in the chromatogram of 09M111-1, these peaks are clearly not observed in the chromatogram of Opale Citrine. The absorption spectra acquired with the PDA detector corresponding to the observed peaks are shown in FIG. 6. The three peaks characteristic to carotenoid compounds (419 nm, 443 nm and 470 nm) were observed in the excerpted absorption spectra. These compounds are presumed to be carotenoids having α-carotene, β-carotene, lutein, violaxanthin or neoxanthin, or their esters thereof, in the skeleton thereof.

(ii) $^1$H-NMR Analysis of Yellow Pigment $^1$H-NMR measurement, which provides a large amount of chemical structure information, was carried out to determine the chemical structures of the carotenoid skeletons of peaks A, C and D characteristically observed for 09M111-1 in FIG. 5.

About 3 g of dried flower petals are required to obtain about 1 mg of sample required for $^1$H-NMR measurement, and a concentration procedure and the like is required. Since carotenoids are susceptible to the occurrence of isomerization and oxygenation reactions, samples are preferably stored sealed in nitrogen under protection from light in the presence of an oxygenation inhibitor such as dibutylhydroxytoluene (BHT). In addition, although $^1$H-NMR measurement of carotenoids is frequently carried out in deuterochloroform, deuterochloroform may generate hydrochloric acid when decomposed, causing acid-unstable C-5,6 epoxy-carotenoids to be converted to C-5,8 epoxy groups by the acid. Since both 09M111-1 and Opale Citrine became discolored in the presence of deuterochloroform, they were clearly determined to contain C-5,6 epoxycarotenoids such as lutein epoxide, violaxanthin or neoxanthin.

Details of sample preparation are described in the following sections (1) extraction of yellow pigment components, (2) isolation of yellow pigment fraction by medium-pressure liquid chromatography, (3) removal of ester-bound fat chains and triacylglycerol by saponification, and (4) analysis of samples dissolved in hexadeuterobenzene.

(1) Extraction of Yellow Pigment Components 2.97 g each of dried flower petals subjected to freeze-drying treatment were dissolved in 100 mL of acetone containing 1% dibutylhydroxytoluene (BHT) followed by stirring for 1 hour at room temperature to extract yellow pigment components. Subsequently, the extract was concentrated to 20 mL under reduced pressure.

(2) Isolation of Yellow Pigment Fraction by Medium-Pressure Liquid Chromatography The concentrated specimens were purified by medium-pressure liquid chromatography (MPLC) in order to concentrate yellow pigment components from the concentrated specimens. The configuration of the MPLC system consisted of the use of the Smart Flash EPCLC AI-580S (Yamazen) for the main unit, and the HI-FLASH ODS-SM (50 μm, Size L 26×100 mm, 35 g, Yamazen) for the separation column. Delivery of the LC mobile phase consisted of using methanol for mobile phase A, using acetone for mobile phase B, setting the binary gradient to 40% mobile phase B from 0 to 3 minutes and subsequently to 100% mobile phase B for the next 24 minutes, and setting the flow rate to 20 ml/min. Eluate for those fractions that eluted from 18 to 23 minutes and that were observed at an absorption wavelength of 450 nm was recovered and subsequently dried to a solid.

(3) Removal of Ester-Bond Fat Chains and Triacylglycerol by Saponification

In the procedures described in the aforementioned sections (1) and (2), triacylglycerol and fat chains of carotenoid esters contained in flower petals impart their complex $^1$H-NMR signals that obstruct analysis of the carotenoid skeleton by NMR. Esters were therefore hydrolyzed by saponification.

Saponification was carried out by adding 10 ml of 5% KOH methanol to the sample dried to a solid in section (2) followed by reacting for 20 minutes at room temperature. After adding 10 ml each of water and dichloromethane and washing the dichloromethane layer with water and saturated saltwater, the solvent was distilled off at 30° C. under reduced pressure. Moreover, the sample was purified by HPLC to obtain a highly pure 1H-NMR sample. Conditions of HPLC purification consisted of use of the LC-10A (Shimadzu) for the liquid feed unit LC pump, use of the SPD-10A (Shimadzu) for the UV-vis detector, and use of the CAPCELL PAK C18 UG120 (20 mm×250 mm, Shiseido) for the separation column. Delivery of the LC mobile phase was carried out by using a 90% aqueous acetonitrile solution at a flow rate of 10 mL/min. Eluate for which absorbance was able to be confirmed while observing at 450 nm using a UV-vis detector was isolated and dried to a solid for use as $^1$H-NMR sample.

(4) $^1$H-NMR Analysis of Samples Dissolved in Hexadeuterobenzene

Figure 7:
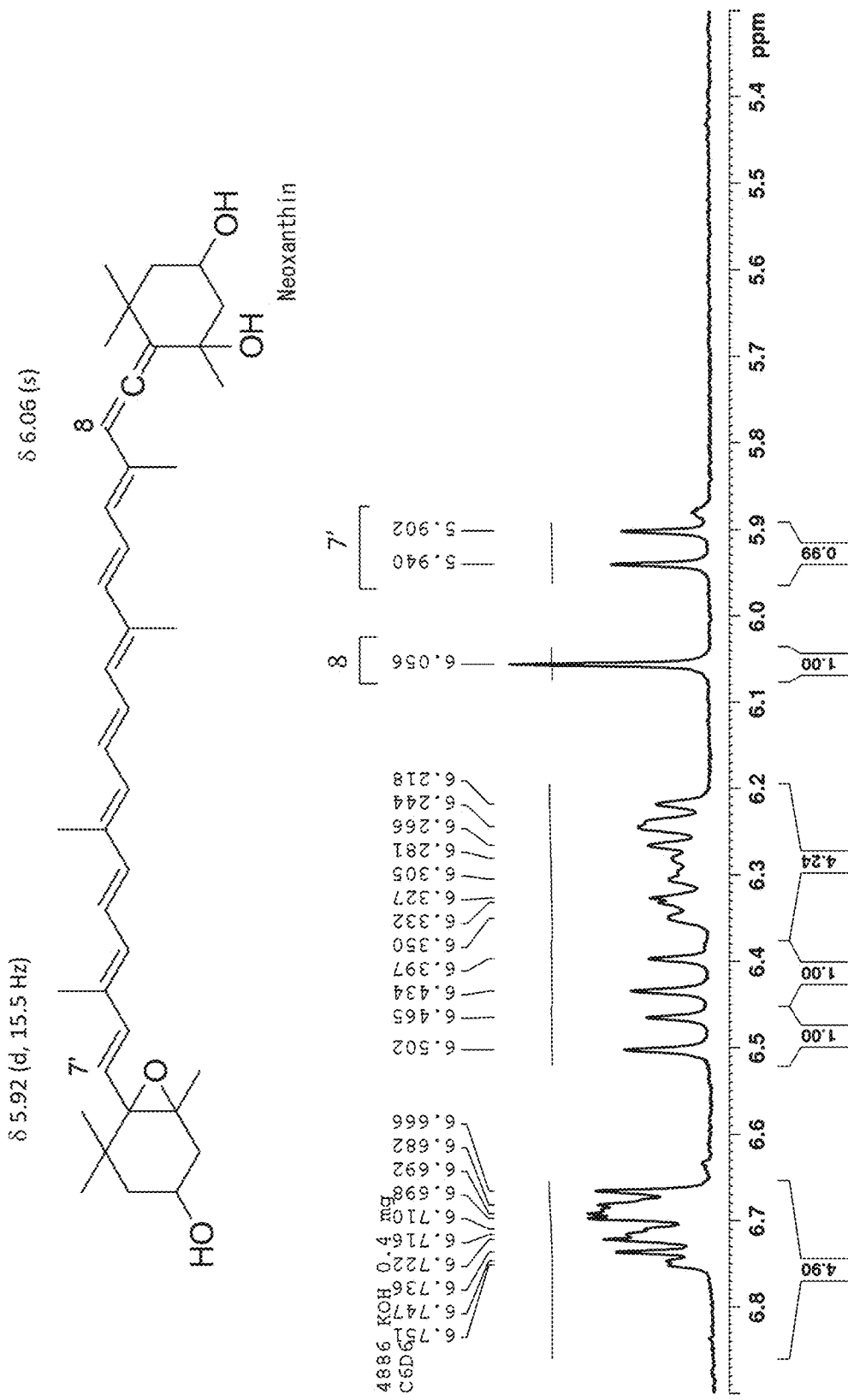
FIG. 7 indicates the $^1$H-NMR spectrum (5.3 ppm to 6.9 ppm) of a *Mandevilla* genus plant of the present invention (09M111-1).
Figure 8:
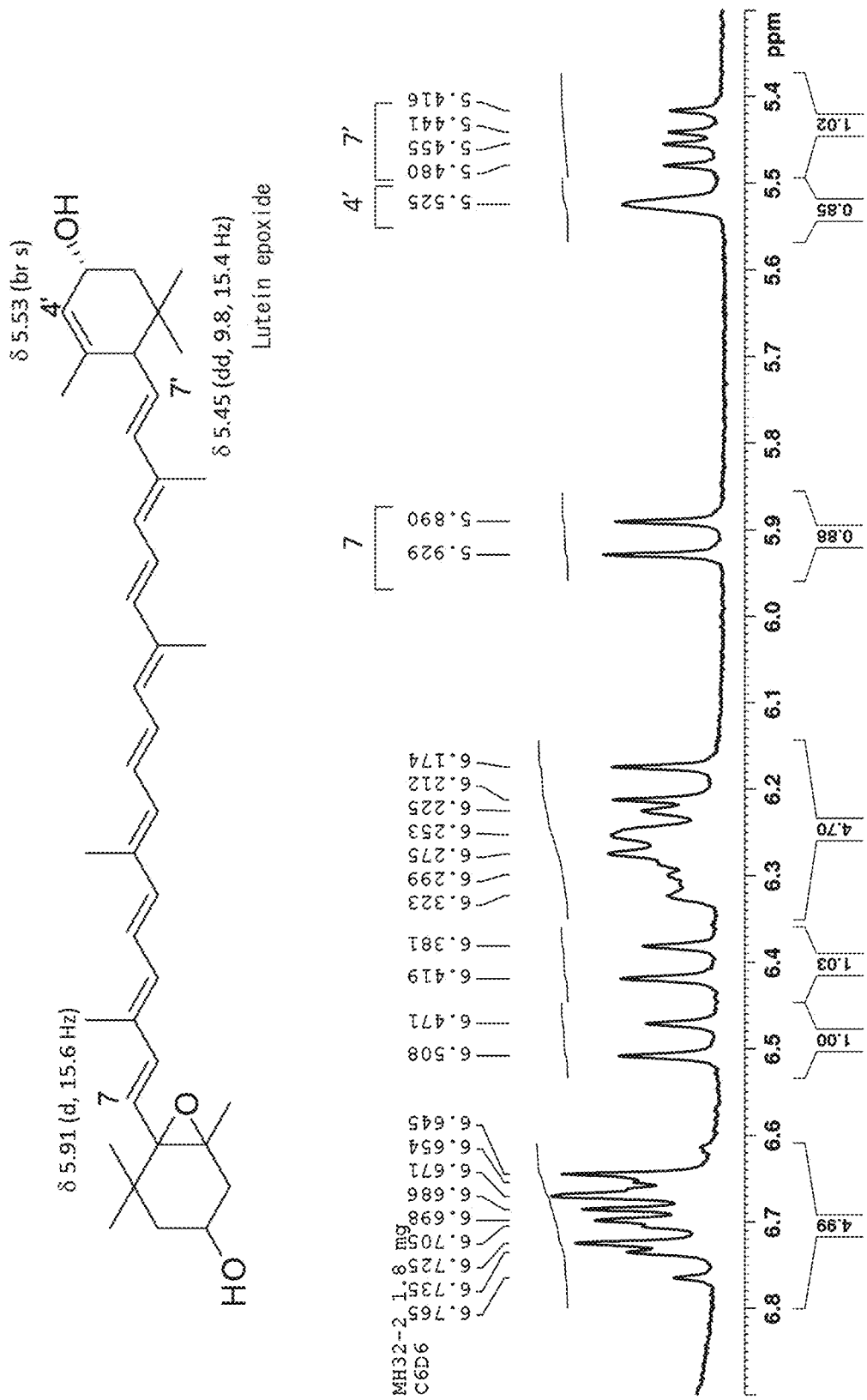
FIG. 8 indicates the 1H-NMR spectrum (5.3 ppm to 6.9 ppm) of an existing *Mandevilla* genus plant (Opale Citrine).

Yellow pigment components following saponification treatment were dissolved in hexadeuterobenzene and subjected to NMR measurement. $^1$H-NMR data was acquired with the AVANCE III HD400 (Bruker). FIG. 7 indicates an enlarged view of the 400 MHz $^1$H-NMR spectrum of 09M111-1 over the range of 5.3 ppm to 6.9 ppm. Chemical structure information of the methine (=CH—) conjugated double bond of carotenoids appears in this drawing. A characteristic signal was observed at 6.06 ppm. This signal indicates the partial structure of the allene structure 8 (C=C=C) in the structural diagram of neoxanthin. On the other hand, based on the NMR signal of Opale Citrine (FIG. 8), a signal was not observed within the range of 6.0 ppm to 6.1 ppm, while signals were observed corresponding to 7 (5.91 ppm), 4' (5.53 ppm) and 7' (5.45 ppm) in FIG. 8. These signals suggested the possibility of lutein epoxide being contained in the sample.

(iii) Identification of Ester Chain Length by LC-APCI-HRMS

Chemical compositions determined by accuracy mass spectrometry measurement were determined in order to identify carotenoid esters corresponding to each peak. Since extracts from flower petals contain compounds other than yellow pigments such as triacylglycerol as well as several types of carotenoid esters, online coupling of mass spectrometry with liquid chromatography separation is an effective means for identifying these compounds. Ionization of mass spectrometry was carried out using atmospheric pressure chemical ionization (APCI), which has been reported to use for mass spectrometry of carotenoids. Mass separation was carried out with the Orbitrap MS, which is an electric field type of Fourier conversion mass spectrometer that allows the obtaining of mass spectra at a resolution of 60,000 or higher for mass separation from triacylglycerol and determination of chemical composition with high accuracy.

Test liquids used for accuracy mass measurement were prepared by weighing out 50.0 mg each of dried flower petals subjected to freeze-drying treatment in glass vials and adding 1.0 mL of extraction solvent in the form of acetone, followed by irradiating with ultrasonic waves with an ultrasonic cleaner (As One, AS52GTU) for 30 minutes at a set temperature of 25° C. to carry out an extraction procedure on yellow pigment components. 0.3 mL of supernatant of the test liquids into which the yellow pigment component had been extracted were filtered with a filter having a pore size of 0.45 μm (Nacalai Tesque, Cosmonice Filter S (solvent type)).

The configuration of the high-performance liquid chromatography-atmospheric pressure chemical ionization-high resolution mass spectrometry system (HPLC-APCI-HRMS) consisted of the use of the Nexera LC-30AD (Shimadzu) for the liquid feed unit LC pump, and the use of the Develosil C30-UG-3 (2.0 mm×100 mm, Nomura Chemical) for the separation column. Delivery of the LC mobile phase consisted of using a mixture of methanol and water (80/20, vol/vol) for mobile phase A, using a mixture of t-butyl methyl ether, methanol and water (78/20/2, vol/vol/vol) for mobile phase B, changing the binary gradient from a mobile phase B concentration of 0% to 100% over the course of 15 minutes, and setting the flow rate to 0.4 mL/min. 10 μL of petal extracts were injected for analysis. Mass spectrometry was carried out using the Orbitrap Elite MS (Thermo Fisher Scientific) equipped with an APCI ion source. Mass spectrometry measurement was carried out by measuring in the positive ion mode at a measurement resolution of 60,000 and m/z ratio within the range of 150 to 2000.

Figure 9:
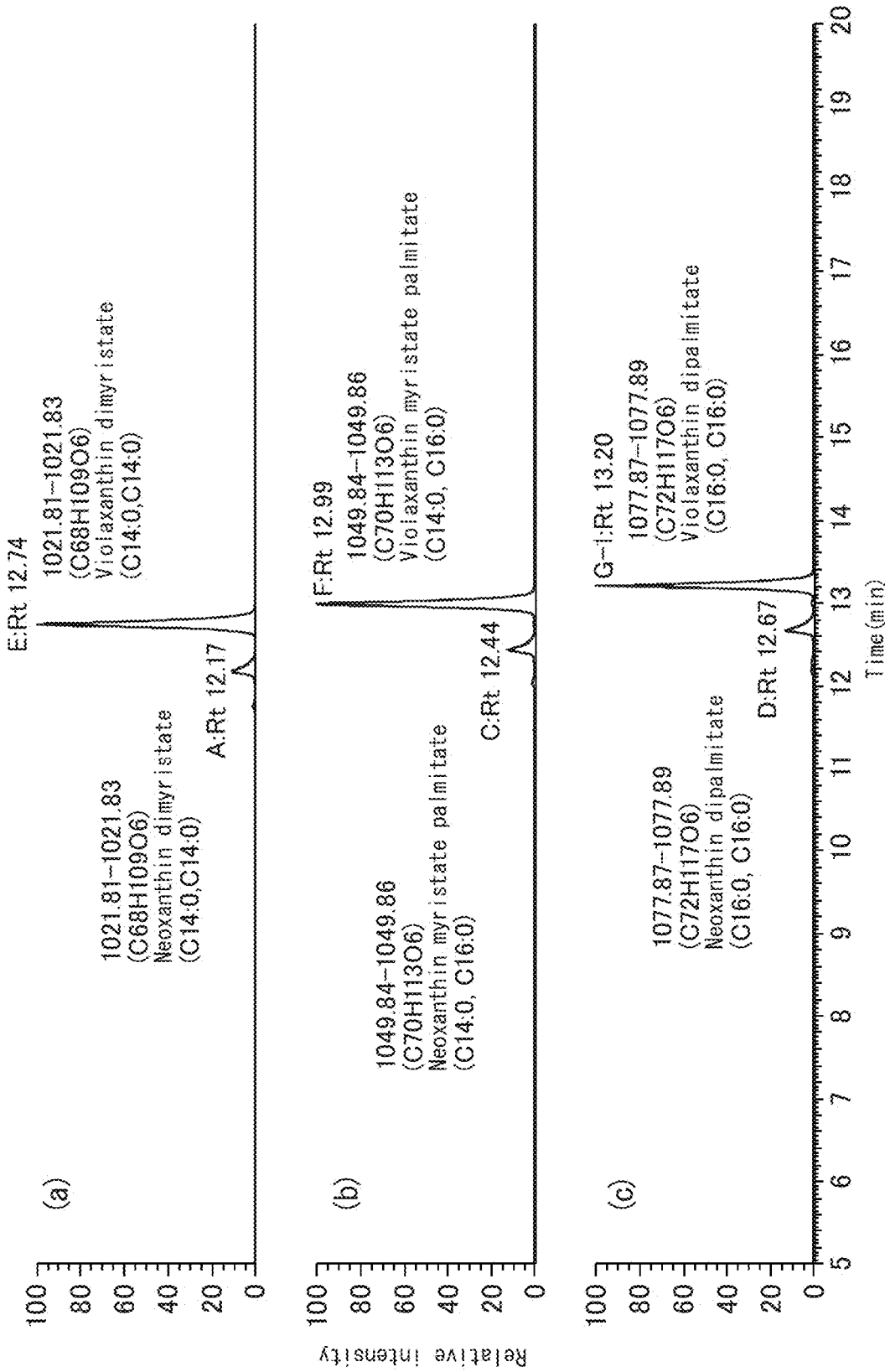
FIG. 9 shows high-resolution mass extracted ion chromatogram of a *Mandevilla* genus plant of the present invention (09M111-1) ((a) m/z 1021.81-1021.83; (b) m/z 1049.84-1049.86; (c) m/z 1077.87-1077.89).
Figure 10:
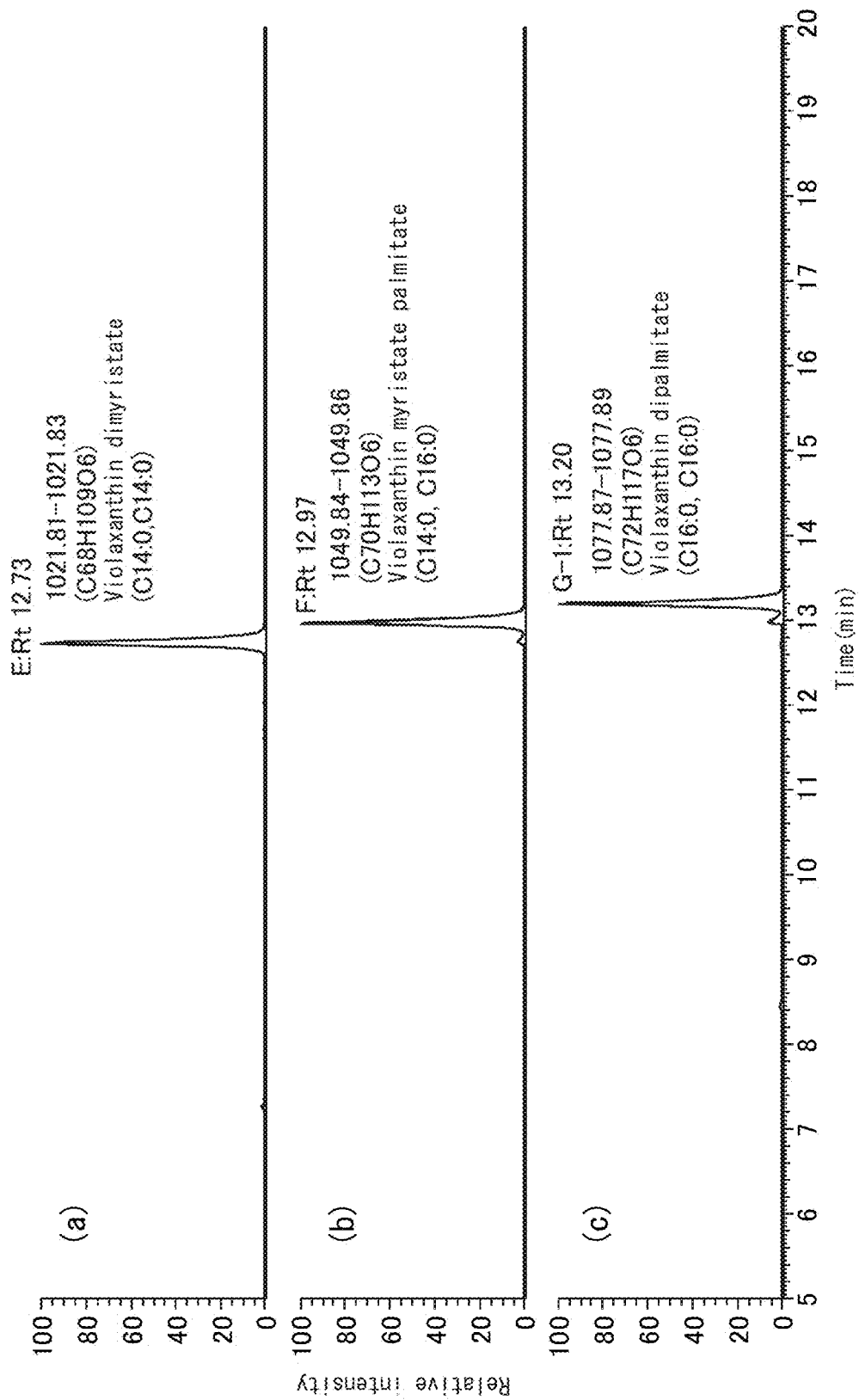
FIG. 10 shows high-resolution mass extracted ion chromatograms of an existing *Mandevilla* genus plant (Opale Citrine) ((a) m/z 1021.81-1021.83; (b) m/z 1049.84-1049.86; (c) m/z 1077.87-1077.89).

Identification of carotenoid compounds from mass spectrometry data was carried out on the basis of (i) absorption spectra obtained by HPLC-PDA, and (ii) mass extracted ion chromatograms of ions corresponding to the theoretical values of the accuracy mass of proton addition ions as determined from the chemical composition when the carotenoid skeleton predicted from $^1$H-NMR analysis had been modified with a fatty acid such as lauric acid, myristic acid, palmitic acid, palmitoleic acid or stearic acid. FIG. 9 indicates the high resolution mass extracted ion chromatogram for 09M111-1 while FIG. 10 indicates the high resolution mass extracted ion chromatogram for Opale Citrine, in which the fatty acids of neoxanthin diester and violaxanthin diester of equal mass correspond to myristic acid and palmitic acid, for (a) m/z 1021.81 to 1021.83, (b) m/z 1049.84 to 1049.86 and (c) m/z 1077.87 to 1077.89. In the chromatogram of 09M111-1 shown in FIG. 9, neoxanthin dimyristate, neoxanthin myristate palmitate, neoxanthin dipalmitate, violaxanthin dimyristate, violaxanthin myristate palmitate and violaxanthin dipalmitate were detected. On the other hand, in the high resolution mass extracted ion chromatogram of Opale Citrine of FIG. 10, only violaxanthin dimyristate, violaxanthin myristate palmitate and violaxanthin dipalmitate were detected.

Figure 11:
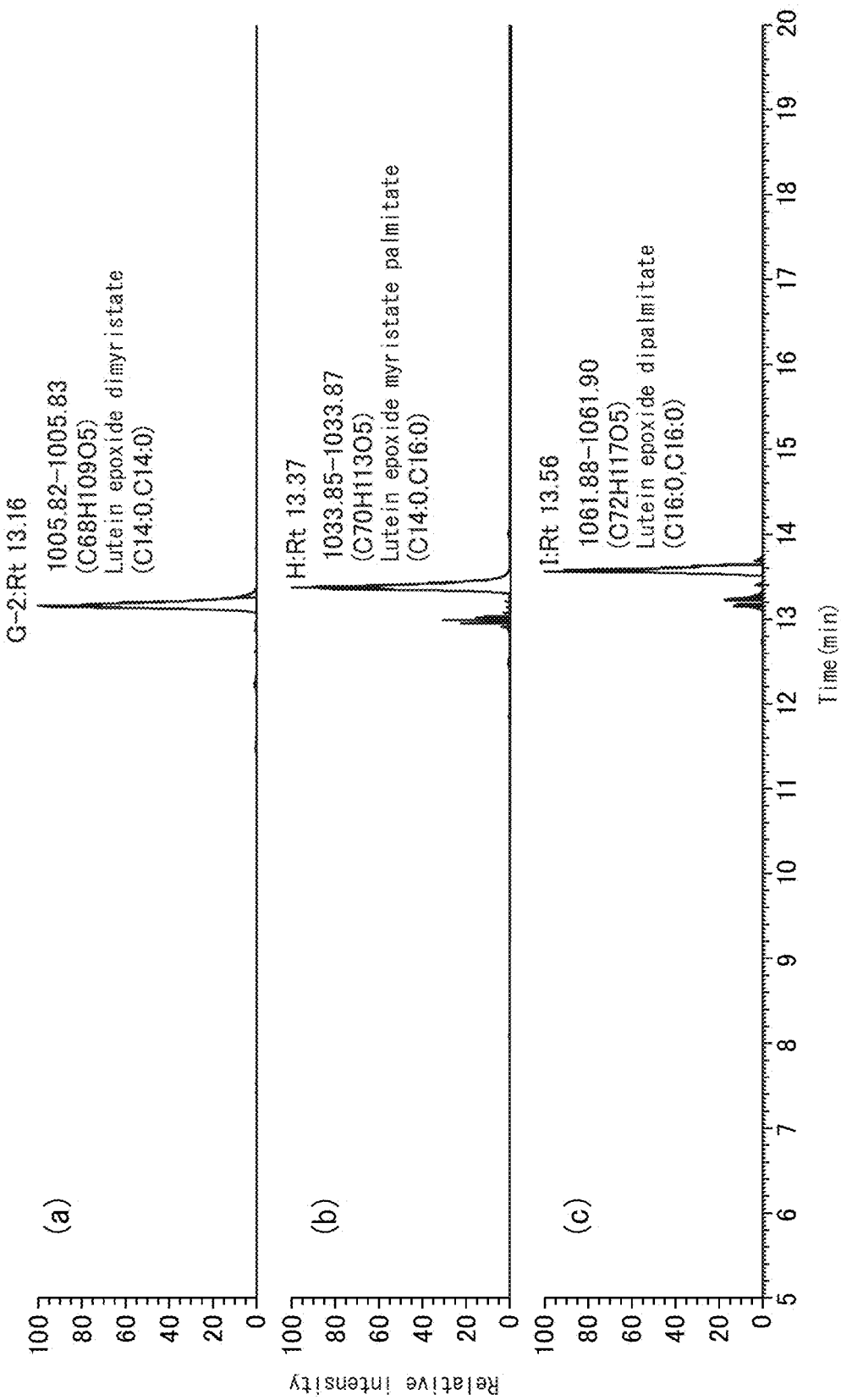
FIG. 11 shows high-resolution mass extracted ion chromatogram of an existing *Mandevilla* genus plant (Opale Citrine) ((a) m/z 1005.82-1005.83; (b) m/z 1033.85-1033.87; (c) m/z 1061.88-1061.90).

FIG. 11 (reference data) indicates the high resolution mass extracted ion chromatogram of Opale Citrine for (a) m/z 1005.82 to 1005.83, (b) m/z 1033.85 to 1033.87, and (c) 1061.68 to 1061.90. The detected peaks correspond to lutein epoxide diester.

As a result of analyzing structure by (i) absorption spectrum with a high-performance liquid chromatography (HPLC)-photodiode array (PAD) detector, (ii) proton nuclear magnetic resonance ('H-NMR) spectrum, and (iii) high resolution mass spectrometry (HRMS) spectrum, peak A was identified as neoxanthin dimyristate having the composition formula $C_{68}H_{108}O_6$, peak C was identified as neoxanthin 3-O-myristate-3'-O-palmitate or neoxanthin 3-O-palmitate-3'-O-myristate having the composition formula $C_{70}H_{112}O_6$, and peak D was identified as neoxanthin dipalmitate having the composition formula $C_{72}H_{116}O_6$.

The invention claimed is:

1. A progeny of a Mandevilla genus plant designated as 09M111-1, which is deposited with the International Patent Organism Depositary (NITE-IPOD) of the National Institute of Technology and Evaluation (NITE) under accession number FERM BP-22298, wherein the progeny contains at least one or more types of carotenoid pigment in the petals, wherein the carotenoid pigment is neoxanthin dimyristate, neoxanthin 3-O-myristate-3'-O-palmitate, neoxanthin 3-O-palmitate-3'-O-myristate, neoxanthin dipalmitate or a combination thereof.

2. The progeny of the Mandevilla genus plant according to claim 1, containing 0.02 mg of cyanidin per 1 g of fresh petals.

3. A vegetative propagant, portion of a plant body, tissue or cells of the progeny of the Mandevilla genus plant according to claim 1.

4. A cut flower of the progeny of the Mandevilla genus plant according to claim 1.

5. A method for producing a Mandevilla genus plant, wherein the method comprises the steps of:
  identifying whether one or more types of carotenoid pigment are present in the petals of a Mandevilla genus plant, wherein the carotenoid pigment is neoxanthin dimyristate, neoxanthin 3-O-myristate-3'-O-palmitate, neoxanthin 3-O-palmitate-3'-O-myristate, neoxanthin dipalmitate or a combination thereof;
  selecting the Mandevilla genus plant if the one or more types of carotenoid pigment is present in the petal; and
  crossing the selected Mandevilla genus plant with another Mandevilla genus plant; or
  growing a vegetative propagant, portion of a plant body, tissue or cells of the selected Mandevilla genus plant.

6. The method according to claim 5, wherein the petal comprises neoxanthin dimyristate, neoxanthin 3-O-myristate-3'-O-palmitate or neoxanthin 3-O-palmitate-3'-O-myristate, and neoxanthin dipalmitate.

7. The method according to claim 5, wherein the Mandevilla genus plant containing at least one or more types of carotenoid pigment in the petals is a Mandevilla genus plant designated as 09M111-1, which is deposited with the International Patent Organism Depository (NITE-IPOD) of the National Institute of Technology and Evaluation (NITE) under accession number FERM BP-22298 or a progeny thereof.

8. The method according to claim 7, wherein the progeny has flower color having an $a^*$ value of −10 to 70 and a $b^*$ value of 0 to 80 in the CIE $L^*a^*b$ color system.

9. The method according to claim 8, wherein the progeny has flower color other than flower color having an $a^*$ value of 0 to 30 and a $b^*$ value of 0 to 5 in the CIE $L^*a^*b$ color system.

10. The method according to claim 7, wherein the progeny has flower color having an $a^*$ value of −5 to 20 and a $b^*$ value of 3 to 70, or having an $a^*$ value of 50 to 70 and a $b^*$ value of 5 to 70 in the CIE $L^*a^*b$ color system.

11. The method according to claim 7, wherein the progeny contains 0.02 mg or more of anthocyanin pigment per 1 g of fresh petals.

* * * * *